United States Patent [19]

Sanderson et al.

[11] Patent Number: 4,810,809

[45] Date of Patent: Mar. 7, 1989

[54] DITERTIARY BUTYL PEROXIDE RECOVERY

[75] Inventors: John R. Sanderson, Leander; Robert A. Meyer, Austin; William A. Smith, Austin; Edward T. Marquis, Austin, all of Tex.

[73] Assignee: Texaco Inc., White Plains, N.Y.

[21] Appl. No.: 945,629

[22] Filed: Dec. 23, 1986

[51] Int. Cl.$^4$ .................. C00F 301/19; C00F 301/32
[52] U.S. Cl. ................................. 549/529; 549/541
[58] Field of Search .......................... 549/529, 541

Primary Examiner—Glennon H. Hollrah
Assistant Examiner—Mark W. Russell
Attorney, Agent, or Firm—Jack H. Park; Kenneth R. Priem

[57] ABSTRACT

It has been discovered in accordance in accordance with the present invention that a tertiary butyl alcohol/ditertiary butyl peroxide azeotrope may be recovered from a product containing tertiary butyl alcohol and ditertiary butyl peroxide by distilling the tertiary butyl alcohol product to obtain an overhead fraction containing substantially all of the ditertiary butyl peroxide/tertiary butyl alcohol azeotrope and other contaminants.

It has been further discovered in accordance with the present invention that the ditertiary butyl peroxide can be recovered from the distillate fraction by extraction with ethylene glycol (e.g., in a countercurrent ethylene glycol extraction tower) to provide a ditertiary butyl peroxide product of any desired degree of purity.

5 Claims, 1 Drawing Sheet

DITERTIARY BUTYL PEROXIDE RECOVERY

BACKGROUND OF THE INVENTION

1. Field of the Invention

This invention relates to the recovery of purified ditertiary butyl peroxide from a feedstock containing a minor amount of ditertiary butyl peroxide. More particularly, this invention relates to a method for the recovery and purification of ditertiary butyl peroxide from a feedstock comprising a major amount of tertiary butyl alcohol and only a minor amount of ditertiary butyl peroxide. Still more particularly, this invention relates to a method wherein ditertiary butyl hydroperoxide is recovered from a feedstock obtained by the oxidation of isobutane to provide a reaction mixture comprising unreacted isobutane, tertiary butyl alcohol, tertiary butyl hydroperoxide and a minor amount of ditertiary butyl peroxide or a reaction mixture obtained by the epoxidation of propylene with tertiary butyl hydroperoxide to propylene oxide and comprising propylene, propylene oxide, tertiary butyl alcohol, unreacted tertiary butyl hydroperoxide, ditertiary butyl peroxide, acetone and other contaminants.

2. Prior Art

It is known to react oxygen with isobutane to form a peroxidation reaction product wherein the principal peroxide that is formed is tertiary butyl hydroperoxide. However, a minor constituent of such a reaction product is ditertiary butyl peroxide, which is a valuable commercial product used, for example, as a high temperature free radical initiator in chemical reactions.

Conventionally, ditertiary butyl peroxide is prepared by the reaction of tertiary butyl alcohol or isobutylene with tertiary butyl hydroperoxide in the presence of an acid catalyst.

The coproduction of propylene oxide together with another hydrocarbon, such as tertiary butyl alcohol, is summarized in an article "Propylene Oxide by the Co-product Process" by Landau et al. (Chem. Tech., October 1979, pp. 602–607).

The process is described in greater detail in Kollar U.S. Pat. Nos. 3,350,422 and 3,351,635 which are directed to the catalytic epoxidation of an olefin by reaction with a hydroperoxide such as tertiary butyl hydroperoxide. When the olefin is propylene and the hydroperoxide is tertiary butyl hydroperoxide, the principal reaction products are propylene oxide and tertiary butyl alcohol.

Herzog U.S. Pat. No. 3,928,393 is directed to an improvement in the Kollar et al. process wherein citric acid is used to minimize iron catalyzed decomposition of the organic hydroperoxide. This patent includes examples directed to the preparation of tertiary butyl hydroperoxide by the reaction of isobutane with oxygen.

Grane U.S. Pat. No. 3,474,151 is also directed to the oxidation of isobutane with oxygen to provide tertiary butyl alcohol and discloses that the reaction mixture contains not only tertiary butyl hydroperoxide, but also ditertiary butyl peroxide. In their U.S. Pat. No. 4,239,926, Grane et al. disclose a method for significantly drying the tertiary butyl alcohol prepared by the oxidation of isobutane, the method involving extractive distillation of the tertiary butyl alcohol product using a specially proportioned blend of xylene, acetone and water as the extractant.

Harvey U.S. Pat. No. 3,449,217 is directed to a method for the recovery of tertiary butyl hydroperoxide from a mixture of tertiary butyl hydroperoxide and tertiary butyl alcohol. However, nothing is said in the patent about the recovery and purification of the ditertiary butyl peroxide.

SUMMARY OF THE INVENTION

Ditertiary butyl peroxide is a stable article of commerce which is used, for example, as a high temperature free radical initiator.

When isobutane is reacted with molecular oxygen a principal product of the reaction is tertiary butyl hydroperoxide. However, minor amounts of other peroxides, including ditertiary butyl peroxide are also formed. Generally speaking, from about 10 to about 100 parts of tertiary butyl hydroperoxide are formed per part of ditertiary butyl peroxide. Minor quantities of other peroxides may also be formed.

In addition, a minor amount of water will be formed, which will normally amount to about 0.5 to 'b wt. % of the reactor effluent. The amount of byproduct water that is produced is a function of the severity of the reaction conditions employed and will tend to increase as the severity of the reaction conditions is increased.

A listing of the components present in a representative reaction product, and their nominal boiling points is given in Table A.

TABLE A

| Component | NBP (°C.) |
|---|---|
| Isobutane | −11.7 |
| Methyl formate | 31.8 |
| Acetone | 56.3 |
| Isobutylene oxide | 60.0 |
| Isobutyraldehyde | 64.1 |
| Methanol | 64.7 |
| Methyl-t-butyl peroxide | 74.2 |
| Isopropyl alcohol | 82.3 |
| Tertiary butyl alcohol | 82.4 |
| Ditertiary butyl peroxide | 111.0 |
| t-butyl-i-pr-peroxide | 124.0 |
| Tertiary butyl formate | 163.8 |

The minor by-products are sometimes difficult to remove. For example, tertiary butyl formate has a higher boiling point than ditertiary butyl peroxide but tends to distill overhead, which suggests that it forms a minimum boiling azeotrope with another component or components.

Tertiary butyl hydroperoxide is useful as a raw material for the manufacture of tertiary butyl alcohol either by decomposition of the tertiary butyl hydroperoxide as such, or by the catalytic reaction of tertiary butyl hydroperoxide with an olefin such as propylene to form an epoxide and tertiary butyl alcohol. When the olefin is propylene, the coproduct is propylene oxide. The reaction conditions used for the conversion of tertiary butyl hydroperoxide, to tertiary butyl alcohol, by either process are such that the ditertiary butyl peroxide normally is not consumed or destroyed and remains in the reaction mixture as an impurity. Only a minor amount of the peroxidation reaction mixture formed by the reaction of molecular oxygen with isobutane will be composed of ditertiary butyl peroxide. However, this minor amount may constitute as much as about 0.5 wt. % of the total peroxidation reaction mixture.

For example, when tertiary butyl hydroperoxide is recovered from the peroxidation reaction mixture obtained by the reaction of molecular oxygen with isobutane, the ditertiary butyl peroxide will also normally be present as a contaminant. Therefore, when the tertiary butyl hydroperoxide is reacted with propylene to form propylene oxide and tertiary butyl alcohol, the ditertiary butyl peroxide will be present in the reaction mixture and in the reaction product.

The product of the reaction of tertiary butyl hydroperoxide with propylene is normally separated into useful components, usually by distillation, to form, for example, sequential distillate fractions composed of unreacted propylene, propylene oxide and tertiary butyl alcohol. The ditertiary butyl peroxide will normally be present in the recovered tertiary butyl alcohol as a contaminant together with other contaminants such as residual tertiary butyl hydroperoxide, acetone, methyl formate, tertiary butyl formate, isopropanol, methanol, etc.

It has been discovered in accordance with the present invention that tertiary butyl alcohol and ditertiary butyl peroxide form an azeotrope containing about equal parts by weight of each component which has a boiling point at 50 mm of mercury of about 24.7° C. It has further been discovered in accordance with the present invention that the tertiary butyl alcohol/ditertiary butyl peroxide azeotrope may be recovered from a product containing tertiary butyl alcohol ditertiary butyl peroxide and other contaminants by distilling the tertiary butyl alcohol product to obtain an overhead fraction containing substantially all of the ditertiary butyl peroxide/tertiary butyl alcohol azeotrope and other contaminants. The distillation cut point for the overhead fraction can vary, but should be a cut point such that the distillate fraction will contain at least about 50 wt. % of tertiary butyl alcohol. When the cut point is selected such that the distillate fraction contains more tertiary butyl alcohol (e.g., from about 50 to about 65% tertiary butyl alcohol), substantially all of the ditertiary butyl peroxide that was initially present in the tertiary butyl alcohol feed to the distillation unit will be present in the distillate fraction.

It has been further discovered in accordance with the present invention that the ditertiary butyl peroxide can be recovered from the distillate fraction by extraction with ethylene glycol (e.g., in a countercurrent ethylene glycol extraction tower) to provide a ditertiary butyl peroxide product of any desired degree of purity. Normally, the ditertiary butyl peroxide raffinate that is obtained by the ethylene glycol extraction step will contain at least a minor amount of tertiary butyl alcohol.

When such is the case, in accordance with the rpesent invention, the ditertiary butyl peroxide raffinate containing the residual quantities of tertiary butyl alcohol is fractionally distilled to provide a light fraction comprising a tertiary butyl alcohol/ditertiary butyl peroxide azeotrope and a heavier fraction consisting essentially of ditertiary butyl peroxide.

Figure 1:
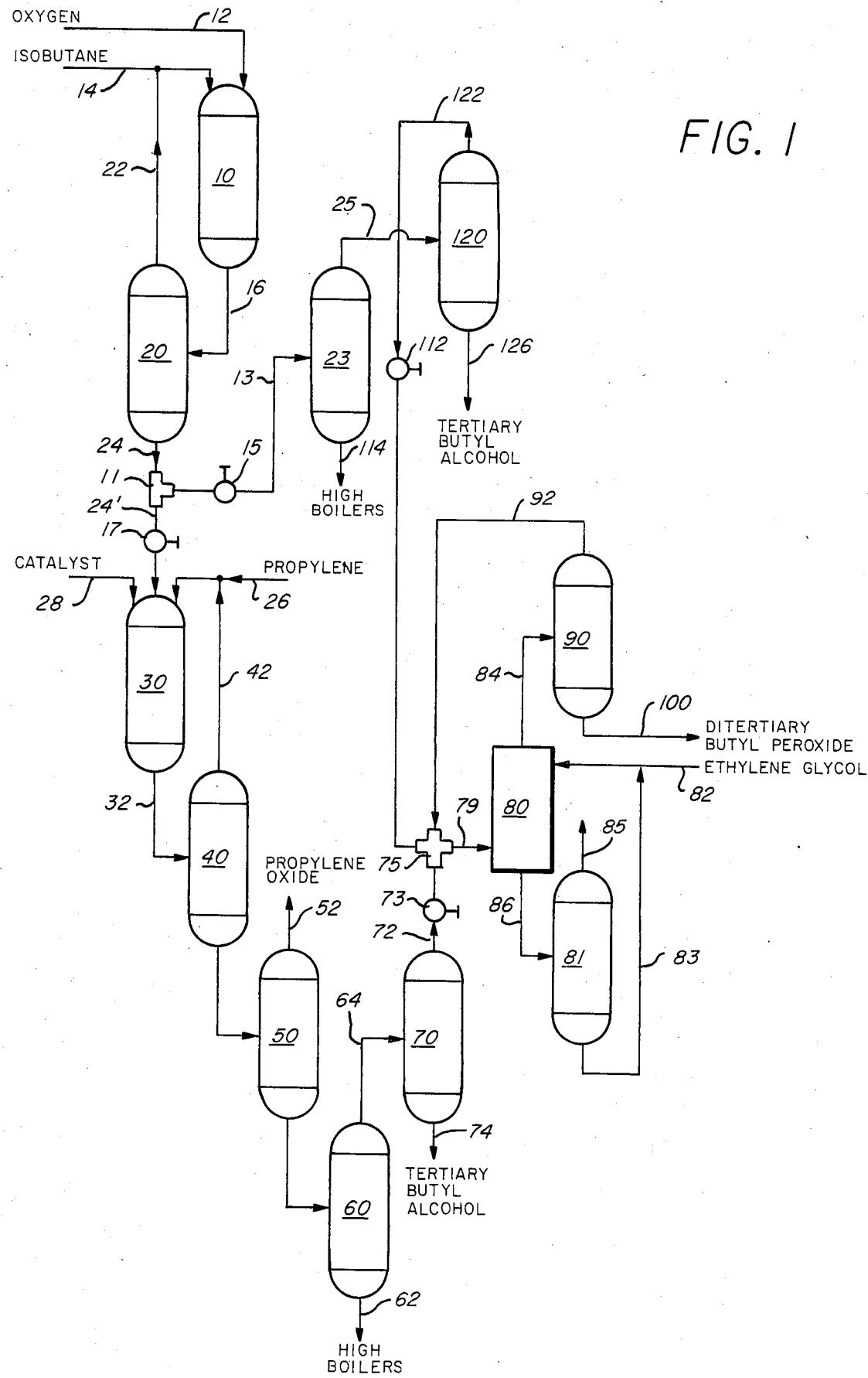
FIG. 1 is a schematic flow sheet with conventional parts omitted showing the general reaction and recovery sequence that is used in the practice of the preferred embodiment of the present invention.

In the drawing, for convenience, the present invention is illustrated in connection both with a process wherein the desired reaction product is tertiary butyl alcohol and also a process wherein propylene oxide is produced as a coproduct together with tertiary butyl alcohol. It will be understood that in normal commercial practice only one of the processes will be used, or if both processes are practiced, that they will be practiced in separate units.

DESCRIPTION OF THE PREFERRED EMBODIMENT

Turning now to FIG. 1, there is shown a schematic flow sheet illustrating a preferred method of practicing the process of the present invention. In the drawing, conventional parts such as valves, pumps, temperature sensors, pressure sensors, heaters, coolers, control and flow regulation apparatus, reboilers, reflux condensers, etc., have been omitted.

In accordance with the present invention, an appropriate reactor 10 is charged with oxygen by way of a charge line 12 and with isobutane and, if desired, a catalyst (e.g., a known molybdenum catalyst) by way of a charge line 14 from appropriate sources (not shown) such as storage tanks. Within the reactor 10, and in accordance with known prior art procedures, the oxygen reacts with a portion of the isobutane to provide a reaction mixture which is discharged from the reactor 10 by way of a discharge line 16. The reaction mixture 16 comprises, for example, unreacted isobutane, tertiary butyl alcohol and minor quantities of other reaction components and byproducts including ditertiary butyl peroxide and may also comprise a significant quantity of tertiary butyl hydroperoxide.

If the only primary product to be manufactured is tertiary butyl alcohol, the reaction conditions used in the reactor 10 will be selected so that the tertiary butyl hydroperoxide is converted directly to tertiary butyl alcohol, as disclosed for example, in Worrell U.S. Pat. No. 4,296,263 or, in the alternative, the decomposition of the tertiary butyl hydroperoxide is accomplished in a separate digestion zone (not shown), as described for example in Grane et al. U.S. Pat. No. 4,294,999 or Grane et al. U.S. Pat. No. 4,296,262.

The reaction mixture 16 is charged to a first distillation zone 20, which may be a simple flash zone, wherein the reaction mixture is separated into a lighter fraction 22 comprising unreacted isobutane which may suitably be recycled to the isobutane charge line 14. A heavier fraction 24 discharged from the first distillation zone 20 comprises tert. butanol and by-products, including tertiary butyl hydroperoxide, ditertiary butyl peroxide, acetone, methanol, ethyl formate, tertiary butyl formate, isopropyl alcohol, etc.

If desired, the cut-point for the distillate fraction 22 may be selected such that a minor amount of tertiary butyl alcohol is taken overhead with the isobutane. If this is done, at least a portion of the by-product water will also be taken overhead, thus partially drying the heavier fraction 24. In this instance, the t-butyl alcohol and water would be charged to a decanter (not shown) and an isobutane rich stream would be recycled from the decanter to the isobutane charge line 14. This will normally be the case if the fraction 24 is to be used as a feedstock for reaction of the tertiary butyl hydroperoxide contained therein with propylene to form propylene oxide and additional tertiary butyl alcohol because it is normally desirable, in this situation, to use a feedstock containing about 0.5 wt. % or less of water.

The heavier fraction 24 is charged to a three-way junction 11. If the fraction 24 is a reaction product to be used primarily for the production of tertiary butyl alcohol (and contains only a minor amount of tertiary butyl hydroperoxide), it is discharged from three-way junction 11 by a branch line 13 controlled by a valve 15 to be processed in a manner to be described.

In accordance with one preferred embodiment of the present invention, the heavier fraction 24 contains a significant amount of tert. butyl hydroperoxide and is discharged from three-way junction 11 by a line 24' controlled by a valve 17 leading to a second reactor 30.

Propylene from a suitable source (not shown) is also charged to reactor 30 by a charge line 26 and an appropriate catalyst (e.g., a propylene glycol solution of a soluble molybdenum catalyst such as molybdenum glycolate), is charged by way of a catalyst charge line 28.

Within the reactor 30, propylene is catalytically reacted with tertiary butyl hydroperoxide, in accordance with known procedures, to provide a reaction mixture which is discharged by way of a discharge line 32 and is composed of unreacted propylene, tertiary butyl alcohol, propylene oxide, and byproducts, including not only the ditertiary butyl peroxide initially charged by way of line 24, but also impurities, principally acetone, methanol, methyl formate, propylene glycol, glycol ethers, etc., formed during the course of the epoxidation reaction. The reaction mixture 32 is charged to a second distillation zone 40, for example, wherein unreacted propylene is recovered overhead by way of a line 42 for recycle to the propylene charge line 26 for the reactor 30 and a bottoms fraction 44 which is charged to a third distillation zone 50.

An overhead propylene oxide fraction 52 is recovered from the distillation zone 50 and the bottom products are discharged by line 54 leading to a fourth distillation zone 60 where the fraction 54 is separated into a bottoms fraction 62 comprising catalyst and other heavy residue which may be purged from the system. In addition, an overhead fraction 64 is obtained which is composed primarily of tertiary butyl alcohol but which also contains the intermediate impurities including ditertiary butyl peroxide and hydroperoxide impurities, acetone, and other oxygenated impurities formed in reactor 30.

In accordance with this embodiment of the present invention, the fraction 64 is charged to a fifth distillation zone 70.

In fifth distillation zone 70 a distillate fraction is obtained containing a tertiary butyl alcohol/ditertiary butyl peroxide azeotrope and comprising about 50 to about 65 wt. % of tertiary butyl alcohol, and substantially all of the ditertiary butyl peroxide, together with other impurities that boil overhead therewith. The distillate fraction is discharged from the fifth distillation zone 70 by a line 72 controlled by a valve 73.

A bottoms fraction 74 composed of tertiary butyl alcohol and residual impurities is recovered from distillation zone 70.

In accordance with the present invention, the fraction 72 is charged to a first four-way junction 75 and then by a feed line 79 to the bottom of an ethylene glycol extraction zone, such as a packed extraction column 80. Ethylene glycol is charged to the column 80 by way of an ethylene glycol charge line 82 for countercurrent contact with the azeotrope feed fraction 79 fed to the bottom of the tower. As a consequence of the countercurrent contact, a raffinate phase 84 is formed which is taken overhead and an extract phase 86 is formed, which is composed of ethylene glycol, tertiary butyl alcohol, and a trace amount of water (e.g., less than 1 wt. %) and minor quantities of other impurities.

The extract may be discharged by the line 86 for further processing.

By way of example, about 100 pounds per hour of a mixture of about 50 wt. % of tertiary butyl alcohol with about 50 wt. % of ditertiary butyl peroxide may be charged to the ethylene glycol extraction tower 80 by line 79 and about 100 pounds per hour of ethylene glycol may be charged to the ethylene glycol extraction tower 80 by line 82. The solvent lean raffinate 84 from the extraction tower 80, in this instance may comprise, for example, about 99 wt. % of ditertiary butyl peroxide, about 0.9 wt. % of tertiary butyl alcohol and about 0.1 wt. % of water. The ethylene glycolrich extract solution 86 discharged from extraction zone 80 by line 86, in this instance, may comprise about 30 wt. % of tertiary butyl alcohol, about 69 wt. % of ethylene glycol, about 0.9 wt. % of water and about 0.1 wt. % of ditertiary butyl peroxide.

The extract phase 86 is composed of ethylene glycol, water, tertiary butyl alcohol and other impurities and may be charged to an extract separation zone 81, which may be a flash drum, a distillation column, etc., where the fraction 86 is separated into a bottoms ethylene glycol fraction 83 that suitably may be recycled to ethylene glycol charge line 82 and a lighter distillate fraction 85 composed of t-butyl alcohol, water and residual impurities is recovered from distillation zone 81.

The raffinate phase 84 from ethylene glycol extraction zone 80 is suitably fed to a sixth distillation zone 90 where it is separated into an overhead distillate fraction comprising a tertiary butyl alcohol/ditertiary butyl peroxide azeotrope 92 which, if desired, may be recycled to first four-way junction 75.

The higher boiling fraction 100 discharged from the sixth distillation zone 90 will be composed primarily of ditertiary butyl peroxide, the degree of purity being, for example, from 85 to 99%, depending upon the efficiency with which the ethylene glycol extraction tower 80 is operated.

The second, third, fourth and fifth distillation zones 40, 50, 60 and 70 may be operated as a multi-stage distillation zone and, in practice, may contain either a greater or a lesser number of distillation towers, depending on the particular distillation engineering design that is used.

In accordance with another embodiment of the present invention, valves 17 and 73 are closed and valves 15 and 112 are opened so that the fraction 24 after being charged to first three-way junction 11 is then charged by line 13 to a seventh distillation zone 23 wherein a lighter tertiary butyl alcohol fraction 25 is obtained. The fraction 25 is comprised principally of tertiary butyl alcohol, but will also contain intermediate impurities including ditertiary butyl peroxide, tertiary butyl hydroperoxide, acetone and other oxygenated impurities formed in the reactor 10. A bottoms fraction comprising catalyst and higher boiling residue components is discharged from seventh distillation zone 23 by line 114 and may be purged from the system.

In accordance with this embodiment of the present invention, the fraction 25 is charged to an eighth distillation zone 120. In eighth distillation zone 120, a distillate fraction 122 is obtained which is composed of a tertiary butyl alcohol/ditertiary butyl peroxide azeotrope comprising about 50 to 65 wt. % of tertiary butyl alcohol and substantially all of the ditertiary butyl peroxide formed in the reactor 10, together with other impurities that boil overhead therewith. The distillate fraction is discharged through line 122 controlled by valve 112 leading to first four-way junction 75.

A tertiary butyl alcohol fraction is recovered from eighth distillation zone 120 by a line 126.

EXAMPLES

In order to illustrate the type of feedstock that may be used to practice the process of the present invention, a feedstock was used obtained by the catalytic reaction of propylene with tertiary butyl hydroperoxide to provide a reaction mixture composed principally of tertiary butyl alcohol, unreacted propylene and unreacted propylene oxide from which both the propylene and propylene oxide had been removed. The resulting product had the composition as set forth in Table I.

TABLE I

Extraction of TBA Distillate[a]

Starting Material

| | |
|---|---|
| Isobutane | 0.344 |
| Methyl Formate | 8.192 |
| Isobutylene Oxide | 0.380 |
| Acetone | 14.359 |
| Isobutyraldehyde | 0.196 |
| Methyl t-Butyl Peroxide | 0.698 |
| Methanol | 1.039 |
| t-Butyl Alcohol | 58.128 |
| t-Butyl Formate/IPA | 5.828 |
| t-Butyl i-Pr Peroxide | 0.393 |
| Di-tert-Butyl Peroxide | 7.782 |

[a]6071-27-20
N.B. No. 6064-85

Turning now to Table I, it will be noted that the starting material that was used was composed principally of tertiary butyl alcohol, but contained a significant quantity of acetone and significant quantities of both methyl formate and ditertiary butyl peroxide. Contaminating quantities of isobutane, isobutylene oxide, isobutyraldehyde, methyl t-butyl peroxide, methanol, a t-butyl formate/isopropyl alcohol doublet and t-butyl isopropyl peroxide were also present in the feed material.

EXAMPLES

Since the principal component of the feed material of the present invention is tertiary butyl alcohol, in order to more easily illustrate the advantage of the present invention, a number of synthetic feedstock fractions were prepared, having the compositions set forth in the examples and composed of mixtures of various amounts of ditertiary butyl peroxide and tertiary butyl alcohol. The starting materials were subjected sequentially to both ethylene glycol extractions under ambient conditions using various parts by weight of the starting material and ethylene glycol for each extraction.

6089-87

Di-tert-butyl peroxide (10.3 g) and tert-butyl alcohol (20.0 g) were extracted with 30.0 g ethylene glycol. Two layers were obtained. Analysis showed the following results:

| | Area % | | |
|---|---|---|---|
| | DTBP | TBA | EG |
| Upper Layer | 73.31 | 22.08 | 3.36 |
| Lower Layer | 19.92 | 48.35 | 31.50 |

The upper layer (3.0 g) was extracted once more with 10.0 g of ethylene glycol. Two layers were again formed. Analysis showed the following results:

| | Area % | | |
|---|---|---|---|
| | DTBP | TBA | EG |
| Upper Layer | 98.17 | 1.08 | 0.04 |
| Lower Layer | 19.92 | 48.35 | 31.501 |

6089-88

100.3 g of a mixture consisting of 40.18% DTBP, 54.84% TBA, and 4.99% water was extracted with 103.3 g EG. The mixture separated into two layers. The GC analyses are shown in the following table:

| | Area % | | | |
|---|---|---|---|---|
| | DTBP | TBA | EG | H₂O |
| Upper Layer | 82.71 | 15.44 | 1.23 | 0.17 |
| Lower Layer | 5.91 | 44.25 | 42.42 | 7.32 |

30.0 g of the upper layer from the first extraction was extracted with 30.0 g EG. The results are below.

| | Area % | | | |
|---|---|---|---|---|
| | DTBP | TBA | EG | H₂O |
| Upper Layer | 96.98 | 2.39 | ? | 0.45 |
| Lower Layer | 1.04 | 19.60 | 74.87 | 4.44 |

20.0 g of the upper layer from the second extraction was extracted with 20.0 g EG. The results follow:

| | Area % | | | |
|---|---|---|---|---|
| | DTBP | TBA | EG | H₂O |
| Upper Layer | 99.04 | 0.38 | 0.02 | 0.04 |
| Lower Layer | 0.357 | 3.94 | 90.38 | 5.28 |

6089-91

20.0 g of a 50% DTBP/50% TBA mixture was extracted with 40.0 g EG. The mixture separated into two layers. The results follow:

| | Area % | | |
|---|---|---|---|
| | DTBP | TBA | EG |
| Upper Layer | 93.31 | 5.80 | 0.35 |
| Lower Layer | 4.19 | 33.42 | 62.23 |

6089-92

20.3 g of a 50% DTBP/50% TBA mixture was extracted with 20.6 g EG. The mixture separated into two layers. The results follow:

| | Area % | | |
|---|---|---|---|
| | DTBP | TBA | EG |
| Upper Layer | 85.70 | 12.35 | 1.30 |
| Lower Layer | 10.37 | 44.09 | 45.28 |

6089-93

20.5 g of a 50% DTBP/50% TBA mixture was extracted with 62.2 g EG. The mixture separated into two layers. The results follow:

| | Area % | | |
|---|---|---|---|
| | DTBP | TBA | EG |
| Upper Layer | 95.50 | 3.82 | 0.19 |
| Lower Layer | 2.66 | 28.98 | 68.21 |

6089-94

30.8 g of a 66.6% DTBP/33.4 % TBA mixture was extracted with 33.4 g EG. The mixture separated into two layers. The results follow:

| | Area % | | |
|---|---|---|---|
| | DTBP | TBA | EG |
| Upper Layer | 91.51 | 7.57 | 0.49 |
| Lower Layer | 4.98 | 37.68 | 57.22 |

The foregoing experiments are presented by way of example only, and are not intended as limitations of the scope of this invention.

Having this described our invention, what is claimed is:

1. In a process wherein a feed material comprising significant amounts of tertiary butyl hydroperoxide and tertiary butyl alcohol and minor amounts of ditertiary butyl peroxide and other impurities is charged to a reactor together with propylene and a soluble epoxidation catalyst and wherein at least a portion of the tertiary butyl hydroperoxide is reacted in said reactor with said propylene to form a reaction product composed of unreacted feed components, propylene oxide, an additional quantity of tertiary butyl alcohol, and impurities, including a minor amount of ditertiary butyl peroxide, the improvement for recovering substantially pure ditertiary butyl peroxide from said reaction product after said reaction product is discharged from said reactor which comprises the steps of:

charging said reaction product to a first distillation zone and separating therein a first unreacted propylene distillate recycle fraction, charging the remaining heavier components of said reaction product from said first distillation zone to a second distillation zone and separating a second propylene oxide distillate product fraction therein, charging the heavier components from said second distillation zone to a third distillation zone and separating a third distillate fraction comprising a major amount of tertiary butyl alcohol and a minor amount of ditertiary butyl peroxide, charging said third distillate fraction from said third distillation zone to a fourth distillation zone and separating a fourth distillate ditertiary butyl peroxide/ tertiary butyl alcohol azeotrope fraction and a heavier tertiary butyl alcohol product fraction therein, charging said fourth distillate ditertiary butyl peroxide/tertiary butyl alcohol azeotrope fraction from said fourth distillation zone to an ethylene glycol extraction zone and resolving said distillate ditertiary butyl peroxide/tertiary butyl alcohol azeotrope fraction therein by ethylene glycol extraction into a raffinate fraction composed principally of ditertiary butyl peroxide and an extract fraction comprising ethylene glycol, ditertiary butyl peroxide and tertiary butyl alcohol, and recovering said second propylene oxide distillate fraction, said heavier tertiary butyl alcohol product fraction and said ditertiary butyl peroxide raffinate fraction.

2. A method as in claim 1 wherein said fourth distillate ditertiary butyl peroxide/tertiary butyl alcohol azeotrope fraction contains from about 50 to about 65wt. % of tertiary butyl alcohol.

3. A method as in claim 2 wherein said first propylene distillate fraction is recycled to said reaction zone.

4. A method for the continuous production of propylene oxide, tertiary butyl alcohol and ditertiary butyl peroxide which comprises the steps of:

a. continuously charging isobutane and oxygen to a first reaction zone and reacting oxygen with a portion of the isobutane therein to provide a first reaction product comprising unreacted isobutane, tertiary butyl alcohol and minor quantities of other reaction components and byproducts including ditertiary butyl peroxide, said ditertiary butyl peroxide being present in the ratio of about 1 part of ditertiary butyl peroxide per 10 to 100 parts of tertiary butyl hydroperoxide, b. continuously charging said first reaction product to a first distillation zone and separating an unreacted isobutane distillate fraction therefrom, c. continuously recyling said unreacted isobutane distillate fraction to said first reaction zone, d. continuously charging the remainder of said first reaction product, comprising principle amounts of tertiary butyl hydroperoxide and tertiary butyl alcohol and a minor amount of ditertiary butyl peroxide, from said first distillation zone to a second reaction zone together with propylene and a soluble epoxidation catalyst and continuously reacting a portion of said propylene with said tertiary butyl hydroperoxide therein to form a second reaction product composed of unreacted components of said first reaction product, propylene, propylene oxide and an additional quantity of tertiary butyl alcohol, e. continuously distilling said second reaction product to obtain a first unreacted propylene distillate fraction, a second propylene oxide distillate product fraction and a third distillate fraction comprising a major amount of tertiary butyl alcohol and a minor amount of ditertiary butyl peroxide, f. and also continuously distilling said third distillate fraction to separate said third distillate fraction into a fourth distillate ditertiary butyl peroxide/tertiary butyl alcohol azeotrope fraction and a heavier tertiary butyl alcohol product fraction, said fourth distillate ditertiary butyl peroxide/tertiary butyl alcohol azeotrope fraction containing from about 50 to about 65 wt. % of tertiary butyl alcohol, and g. continuously charging said fourth ditertiary butyl peroxide/tertiary butyl alcohol distillate azeotrope fraction to an ethylene glycol extraction zone and resolving said fourth ditertiary butyl peroxide/tertiary butyl alcohol distillate azeotrope fraction by ethylene glycol extraction therein into a raffinate fraction composed principally of ditertiary butyl peroxide and containing a minor amount of tertiary butyl alcohol and an extract fraction comprising ethylene glycol, ditertiary butyl peroxide and tertiary butyl alcohol, h. continuously recycling said first unreacted propylene distillate fraction to said second reaction zone, and i. continuously recovering said second propylene oxide distillate product fraction, said heavier tertiary butyl alcohol product fraction and said ditertiary butyl peroxide raffinate fraction.

5. A method as in claim 4 wherein said extract fraction is charged to an extract separation zone and resolved therein into an ethylene glycol bottoms fraction and a lighter overhead fraction comprising tertiary butyl alcohol and water and wherein said ethylene glycol fraction is recycled to said ethylene glycol extraction zone, wherein said raffinate fraction is further distilled to provide a tertiary butyl alcohol/ditertiary butyl peroxide azeotrope recycle fraction and a higher boiling ditertiary butyl peroxide fraction containing from about 85% to about 99% of ditertiary butyl peroxide, and wherein said tertiary butyl alcohol/ditertiary butyl peroxide recycle fraction is recycled to said ethylene glycol extraction zone.

* * * * *